United States Patent
Greene et al.

(10) Patent No.: US 7,842,456 B2
(45) Date of Patent: *Nov. 30, 2010

(54) REAGENTS, KITS AND METHODS FOR IMMUNODETECTION OF EPITOPES ON MOLECULES

(75) Inventors: Mark I. Greene, Penn Valley, PA (US); Hongtao Zhang, Paoli, PA (US); Xin Cheng, Wallingford, PA (US)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 808 days.

This patent is subject to a terminal disclaimer.

(21) Appl. No.: 10/589,811

(22) PCT Filed: Feb. 18, 2005

(86) PCT No.: PCT/US2005/005444

§ 371 (c)(1),
(2), (4) Date: Jun. 8, 2007

(87) PCT Pub. No.: WO2005/081908

PCT Pub. Date: Sep. 9, 2005

(65) Prior Publication Data

US 2008/0020374 A1  Jan. 24, 2008

Related U.S. Application Data

(60) Provisional application No. 60/546,225, filed on Feb. 20, 2004.

(51) Int. Cl.
*C12Q 1/68* (2006.01)
*C12P 19/34* (2006.01)

(52) U.S. Cl. .................. 435/6; 436/501; 435/91.2

(58) Field of Classification Search .......... 435/6, 435/91.2, 91.52, 7.1, 501
See application file for complete search history.

(56) References Cited

U.S. PATENT DOCUMENTS

| | | | |
|---|---|---|---|
| 5,334,702 A | | 8/1994 | Greene et al. |
| 5,436,134 A | | 7/1995 | Haugland et al. |
| 5,627,027 A | * | 5/1997 | Waggoner .................. 435/6 |
| 5,663,144 A | | 9/1997 | Greene et al. |
| 5,665,539 A | | 9/1997 | Sano et al. |
| 5,728,525 A | | 3/1998 | Conrad |
| 5,919,764 A | | 7/1999 | Greene et al. |
| 5,922,553 A | | 7/1999 | Eberwine et al. |
| 6,022,523 A | | 2/2000 | Degrado et al. |
| 6,140,471 A | | 10/2000 | Johnson et al. |
| 6,172,197 B1 | | 1/2001 | Mccafferty et al. |
| 6,197,599 B1 | | 3/2001 | Chin |
| 6,207,378 B1 | * | 3/2001 | Yamane et al. .................. 435/6 |
| 6,225,447 B1 | | 5/2001 | Winter et al. |
| 6,291,650 B1 | | 9/2001 | Winter et al. |
| 6,743,592 B1 | | 6/2004 | Greene et al. |
| 7,045,286 B2 | | 5/2006 | Greene et al. |
| 7,115,371 B2 | * | 10/2006 | Eberwine .................. 435/6 |
| 7,341,831 B2 | * | 3/2008 | Greene et al. .................. 435/6 |
| 7,361,464 B2 | * | 4/2008 | Greene et al. .................. 435/6 |
| 7,524,628 B2 | * | 4/2009 | Greene et al. .................. 435/6 |
| 2002/0058800 A1 | * | 5/2002 | Kingsbury et al. .......... 536/23.5 |

FOREIGN PATENT DOCUMENTS

| | | |
|---|---|---|
| CA | 2393703 | 6/2001 |
| JP | 05-149949 | 6/1993 |
| JP | 2001/13139 | 1/2001 |
| WO | WO98/22624 | 5/1998 |
| WO | WO02/08757 | 1/2002 |
| WO | WO02/066980 | 8/2002 |

OTHER PUBLICATIONS

U.S. Appl. No. 09/977,716, Mark Greene et al.
Felix, A.M., "Applications of BOP reagent in solid phase synthesis", Int. J. Pep. Prot. Res. 1988 31:231-238.
Giralt, E. and Andreu eds, *In Peptides*, ESCOM, Leiden, The Netherlands 1991,131-133.
Hendrickson et al., "High sensitivity multianalyte immunoassay using covalent DNA-labeled antibodies and polymerase chain reaction," *Nucleic Acids Research* (1999), 23 (3): 522-529.
Hruby, "Conformational restrictions of biologically active peptides via amino acid side chain groups," *Life Sci.* (1982) 31: 189-199.
Leone et al., "Molecular beacon probes combined with amplification by NASBA enable homogeneous, real-time detection of RNA," *Nucleic Acids Res.* (1998), 26 (9): 2150-2155.
Murali et al., "Structure-based design of immunologically active therapeutic peptides," *Immunol. Res.* (1998) 17: 163-169.

(Continued)

*Primary Examiner*—Kenneth R. Horlick
*Assistant Examiner*—Joyce Tung
(74) *Attorney, Agent, or Firm*—Woodcock Washburn, LLP

(57) ABSTRACT

Methods for detecting and/or quantifying molecules expressing a selected epitope in a sample are disclosed. Methods for profiling proteins in a cell lysate are also disclosed. Kits for detecting and/or quantifying molecules expressing a selected epitope in a sample and kits for profiling proteins in a cell lysate are also disclosed.

6 Claims, 5 Drawing Sheets

OTHER PUBLICATIONS

Ploux, 0. et al., "Cyclization of peptides on a solid support. Application to cyclic analogs of substance P ," *Int. J. Pep. Prot. Res.* (1987), 29: 162-169.

Prasad et al., "Contrasting solution conformations of peptides containing alpha,alpha-dialkylated residues with linear and cyclic side chains," *Biopolymers* (1995) 35: 11-20.

Porstmann, T. et al., "Enzyme immunoassay techniques. An overview," *J Immunol Methods*. (1992), 150(1-2):5-21.

Portsmann, B. et al., "Which of the commonly used marker enzymes gives the best results in colorimetric and fluorimetric enzyme immunoassays: horseradish peroxidase, alkaline phosphatase or beta-galactosidase?" *J Immunol Methods* (1985), 79(1):27-37.

Reichmann et al., "Expression of an antibody Fv fragment in myeloma cells," *J. Mol. Biol.* (1988), 203: 825-828.

Romani, S. et al., "Synthesis of the trypsin fragment 10-25/75-88 of mouse nerve growth factor. II. The unsymmetrical double chain cystine peptide," *Int. J. Pep. Prot. Res.* (1987), 29: 107-117).

Saragovi et al., "Design and synthesis of a mimetic from an antibody complementarity-determining region," *Science* (1991), 253: 792-795.

Schiller et al., "Synthesis of side-chain to side-chain cyclized petide analogs on solid supports," *Int. J. Pep. Prot. Res.* (1985), 25: 171-177.

Schweitzer et al., "Inaugural article: immunoassays with rolling circle DNA amplification: a versatile platform for ultrasensitive antigen detection," *Proc Natl Acad Sci U S A.* (2000), 97(18):10113-9.

Sheppard, R. C., "Acid-labile resin linkage agents for use in solid phase peptide synthesis ," *Int. J. Peptide Res.* (1982), 20: 451-454.

Skerra and Pluckthun, "Assembly of a functional immunoglobulin Fv fragment in *Escherichia coli*," *Science* (1988), 240:1038-1044.

Harrison et al. United States Biochemical Pharma. Ltd. (Europe), Watford, United Kingdom), 1996.

Tan et al., "Molecular beacons: a novel DNA probe for nucleic acid and protein studies," *Chemistry* (2000), 6: 1107-1111.

Tannous et al., "T7 RNA polymerase as a self-replicating label for antigen quantification," *Nucleic Acids Res* (2002), 30(24):e140.

Williams et al., "Development of biologically active peptides based on antibody structure," *Proc. Natl Acad. Sci.* USA (1989), 86: 5537-5541.

\* cited by examiner

REAGENTS, KITS AND METHODS FOR IMMUNODETECTION OF EPITOPES ON MOLECULES

CROSS-REFERENCE TO RELATED APPLICATIONS

This application is a national stage application of PCT International Application PCT/US2005/005444, filed Feb. 18, 2005, which claims priority to U.S. Provisional Patent Application 60/546,225, filed Feb. 20, 2004.

This application claims priority to U.S. Provisional Application Ser. No. 60/546,225, filed Feb. 20, 2004, which is incorporated herein by reference. This application is a related to U.S. patent Ser. No. 09/977,716 filed Oct. 15, 2001, U.S. patent Ser. No. 09/783,896, filed Feb. 15, 2001 and U.S. patent application Ser. No. 09/624,946, filed Jul. 25, 2000 which are each incorporated herein by reference.

FIELD OF THE INVENTION

The present invention relates to methods of detecting epitopes on molecules using antibodies linked to nucleic acid templates suitable for use in RNA amplification application whereby the amplification product is stained with a fluorescent dye in order to detect and quantify it. The invention further relates to reagents and kits useful for practicing the method.

BACKGROUND OF THE INVENTION

Traditional methodologies for protein detection and quantification include 2-D gel electrophoresis, mass spectrometry and antibody binding. Each methodology has been used to quantify protein levels from relatively large amounts of tissue, yet each suffers from a lack of sensitivity.

The detection of low abundance antigens and their modifications is the key to understanding the function of many regulatory proteins that are critical for cellular events in the body as well as for the clinical diagnosis of infections and other pathological conditions. Limitations of immunologically detecting antigens relate to the concentration of the antigen and the affinity of the antibodies. Generally, monoclonal antibodies with higher affinity are able to detect antigens at lower concentrations. However the sensitivity of using antibody in detection is limited by detection of the bound antibody. Barriers to detection can be overcome if amplification of the binding signal of rare interactions could be generated in a linear and consistent manner.

The detection limit for ELISA type assays ranges from 0.1-50 ng/ml, depending upon the affinity of antibodies, especially the capture antibody used. In a "sandwich" or two-site ELISA assay, the use of higher affinity antibody to capture antigen correlates with higher sensitivities (Porstmann, T. & Kiessig, S. T. Enzyme immunoassay techniques. An overview. *Journal of Immunological Methods*. 150, 5-21 (1992)). The detection antibody is often conjugated to enzymes, usually peroxidase or alkaline phosphatase, to amplify the signals. Replacing calorimetric products with fluorogenic substrates only slightly improves the sensitivity of the assay by less than one order of magnitude (Porstmann, B., Porstmann, T., Nugel, E. & Evers, U. Which of the commonly used marker enzymes gives the best results in colorimetric and fluorimetric enzyme immunoassays: horseradish peroxidase, alkaline phosphatase or beta-galactosidase? *Journal of Immunological Methods*. 79, 27-37 (1985)). In addition, increased background is generally associated with improved sensitivity of ELISA assays using peroxidase or alkaline phosphatase as well as other non-linear enzymes.

Improvement of the ability to monitor proteins, lipids, sugars and metabolite levels and their modifications is needed for cell biology and medicine. A variety of technologies have been employed to improve the sensitivity of detecting these molecules. Recent examples of detection methods include immuno-PCR, RCA and immuno-aRNA.

Immuno-PCR (U.S. Pat. No. 5,665,539, which is incorporated herein by reference) combines the polymerase chain reaction (PCR) technology with conventional detection methods to increase the sensitivity to detect protein. However, a major limitation of immuno-PCR lies in the non-linear amplification ability of PCR reaction, which limits this technique as a quantitative detection method. Thus, this method provides no direct correlation between the amount of signal and the amount of protein present.

A relatively isothermal rolling circle DNA amplification technique (RCA; Schwietzer et al., Proc. Natl. Acad. Sci. USA 97, 10113, 2000), which is incorporated herein by reference) provides an improvement over immuno-PCR as this technique overcomes some of the quantitation problems associated with immuno-PCR. Rolling-circle amplification (RCA) has also been termed immunoRCA. The amplified signal (single strand DNA) stays with the antigen-antibody complex. ImmunoRCA is an attractive approach for protein microarrays. Femtomolar sensitivity was described for the immunoRCA approach but the actually detection sensitivity of cytokines studied with immunoRCA ranged from 1~1000 pg/ml, a level comparable to already available ELISA detection.

Tannous et al (*Nucleic Acids Research*. 30, e140 (2002)) reported an antigen quantification system that used T7 RNA Polymerase. In their system, T7 RNA Polymerase was complexed with a detection antibody and a DNA template was supplied for amplification. Since the amplified RNA encoded either T7 RNA polymerase or luciferase, an in vitro translation system was then employed to produce enzymes and the final enzyme activity reflected the original antigen concentration.

U.S. Pat. No. 5,922,553, which is incorporated herein by reference, discloses a method for quantifying levels of a selected protein via a technique referred to as immuno-aRNA. In this method, a first antibody targeted to a selected protein is immobilized to a solid support. The support is then contacted with the selected protein so that the selected protein is immobilized to the first antibody. The solid support is then contacted with a RNA promoter-driven cDNA sequence covalently coupled to a second antibody targeted to the selected protein so that the second antibody binds to the bound selected protein. The amount of selected protein is determined by quantifying levels of the promoter driven cDNA sequence covalently coupled to the bound second antibody via an amplified RNA technique. In a preferred embodiment, a T7 promoter driven cDNA sequence is covalently coupled to the second antibody. Accordingly, the antigen of interest is captured by the plate-associated antibody and detected by antibodies directly coupled with double stranded oligonucleotide that accommodates the attachment of the T7 RNA polymerase enzyme. The interaction of T7 leads to the production of RNA species that is monitored with labeled nucleotide. The original concentrations of antigens are determined by auto-radiographic analyses of the RNA species after electrophoresis. While detection sensitivity is high due to the combination of T7 RNA polymerase amplification and use of radioactive isotopes, it also had significant drawbacks. Labeling the amplification products (RNA) with radioisotope and separation of the RNA species with electrophoresis creates a set of lengthy and often difficult steps that preclude widespread usage. Covalent glutaraldehyde coupling conditions are intrinsically variable and have an unpredictable effect on antibody affinity and function.

Single chain fragments as well as exocyclic peptide based complementarity determining region (CDR) subunits have been found to be useful in this immuno-aRNA technique. Further, it has been found that PCR, as well as amplified RNA techniques, can be used to quantify the promoter driven cDNA sequence covalently coupled to the bound single chain fragment or CDR subunit. The use of smaller antibody binding units and fragments coupled with the already existing large single chain or cyclic peptide libraries and the use of robotic assistance renders this method widely useful for both medicinal and research purposes. Furthermore, a single third detector species can be coupled with double-stranded DNA and bound to either the single chain Fv or the CDRs, rendering detection uniform and simple.

SUMMARY OF THE INVENTION

The present invention relates to methods for detecting and/or quantifying molecules expressing a selected epitope in a sample. The methods comprise immobilizing a molecule that expresses a selected epitope in a sample to a solid support. The solid support is contacted with a molecule that specifically binds to the selected epitope, streptavidin and a biotinylated oligonucleotide. The molecule that specifically binds to the selected epitope may be a biotinylated monoclonal antibody, a biotinylated FAb, a biotinylated F(Ab)$_2$, a biotinylated humanized or chimeric antibody preferably including a human Fc, a biotinylated antibody, a biotinylated FAb, biotinylated F(Ab)$_2$, a biotinylated single chain Fv, a biotinylated constrained epitope specific CDR, a biotinylated CDR mimetic, a biotinylated engineered CDR structure, an antibody that comprises a universal epitope, a FAb that comprises a universal epitope, a F(Ab)$_2$ that comprises a universal epitope, a single chain Fv that comprises a universal epitope, a constrained epitope specific CDR that comprises a universal epitope, a CDR mimetic that comprises a universal epitope, or a engineered CDR structure that comprises a universal epitope. If the molecule that specifically binds to the selected comprises a universal epitope, the solid support is additionally contacted with a biotinylated molecule that binds to the universal epitope. The biotinylated molecule that binds to the universal epitope is a biotinylated monoclonal antibody, a biotinylated FAb, a biotinylated F(Ab)$_2$, a biotinylated humanized or chimeric antibody preferably including a human Fc, a biotinylated single chain Fv, a biotinylated constrained epitope specific CDR, a biotinylated CDR mimetic, or a biotinylated engineered CDR structure. According to the invention, the molecule that specifically binds to the selected epitope binds to the selected epitope of the molecule immobilized to the solid support. If it is biotinylated it binds to the streptavidin which binds to the biotinylated oligonucleotide that comprises an RNA polymerase promoter. If it comprises a universal epitope, to the biotinylated molecule that binds to the universal epitope which the streptavidin that binds to the biotinylated oligonucleotide that comprises an RNA polymerase promoter. RNA amplification is then performed using the oligonucleotide as a template to produce an RNA amplification product. The RNA amplification product is contacted with a fluorescent dye that stains the RNA amplification product and the fluorescence emitted from the stained RNA amplification product is detected or quantified. In some preferred embodiments, the oligonucleotide is double stranded DNA having at least 500 base pairs. In some preferred embodiments, the oligonucleotide comprises an RNA polymerase termination sequence. Preferably, the oligonucleotide comprises a T7 RNA polymerase promoter and a T7 RNA polymerase termination sequence.

Another aspect of the present invention provides a method for profiling proteins in a cell lysate. The method comprises contacting a lysate with a mixture of molecules bind to different epitopes. The different molecules are linked to different oligonucleotides. When used in RNA amplification, the different oligonucleotides present, which correspond to different epitopes on molecules present in the lysate, produce different RNA amplification products that can be distinguished to determine the profile of the lysate.

The present invention provides kits for practicing the methods of the invention. The kits comprise the various reagents necessary to perform the methods.

DETAILED DESCRIPTION OF THE INVENTION

Figure 1:
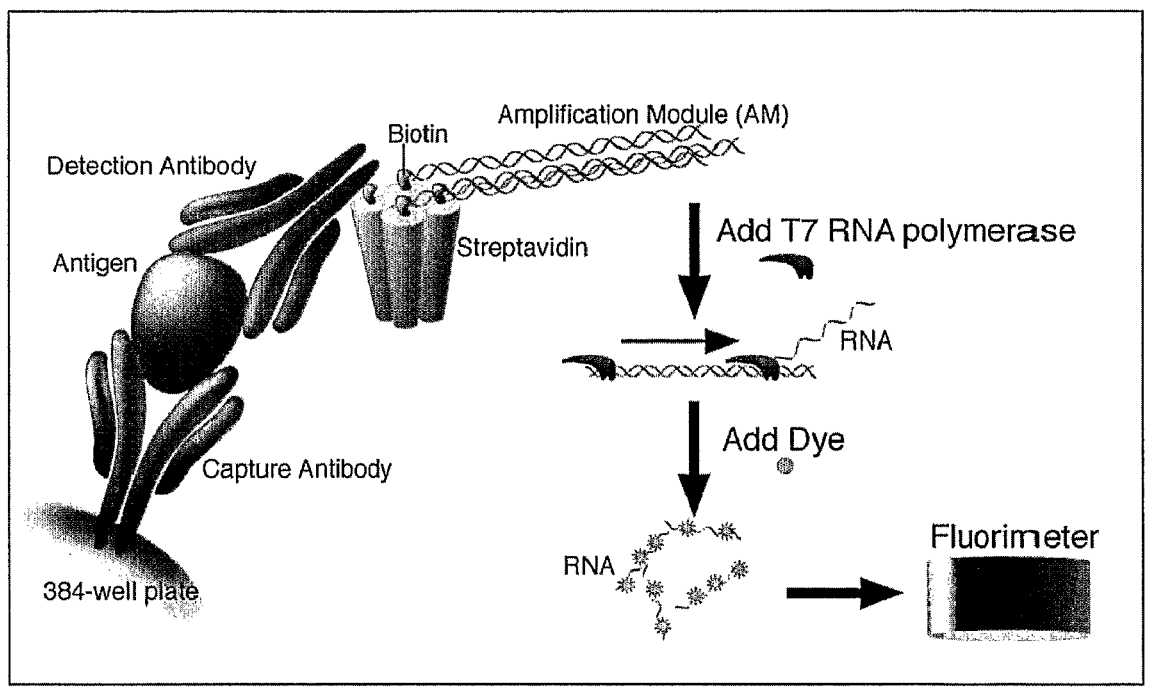
FIG. 1 provides an illustration of a preferred embodiment of the invention (FACTT). The capture antibody first binds the antigen of interest (Ag) from the sample. A detection antibody, which binds to a distant, non-overlapping epitope in the antigen, is biotinylated and linked to a biotin-double-stranded DNA template through streptavidin. T7 RNA polymerase is then used to linearly amplify, from the DNA template, many copies of RNA product, the amount of which is indicative of the original amount of antigen in the sample.

The present invention relates to improved methods for detecting and/or quantifying levels of molecules that comprise a specific epitope and reagents, systems and kits for performing these improved methods. According to some aspects of the invention, nucleic acid molecules that are used as templates in RNA amplification protocols comprise at least 500 bp. According to some aspects of the invention, nucleic acid molecules that are used as templates in RNA amplification protocols comprise a T7 promoter at the 5' end and a T7 terminator sequence art the 3' end. According to some aspects of the invention, nucleic acid molecules that are used as templates in RNA amplification are biotinylated as are the antibodies, FAb, F(Ab)$_2$, Fv antibody fragments, CDRs, CDR mimetics and engineered CDR structures that are linked to the template. The linkage of the two biotinylated components is achieved by a streptavidin bridge.

According to the invention, the molecule that comprises the specific epitope to be detected is preferably immobilized to a solid support or surface. In some embodiments, the molecule is immobilized by use of an anchor that binds to the molecule at a site other than the epitope to be detected. In such embodiments, the anchor is immobilized to the solid support. In some embodiments, the anchor is an antibody, FAb, F(Ab)$_2$, Fv antibody fragment, CDR, CDR mimetic and engineered CDR structure. In some embodiments, the solid support is a glass slide, chip, test tube or well of a multi-well plate such as a 96- or 384-well plate. In a preferred embodiment, the epitope anchor is bound to a designated spot on the surface. For example, the surface may comprise a chip and the epitope anchor is bound to a defined spot on the chip. In one embodiment, the epitope anchor is deposited onto a surface or plate with the aid of a pipettor or similar device which permits application at a single site. The surface with the bound epitope anchor is then contacted with a sample suspected of containing molecules expressing the selected epitope so that the molecule binds to the epitope anchor. In another embodiment, the molecule is attached to a surface directly, without the use of an epitope anchor.

In some embodiments, the molecule is a protein, carbohydrate, or glycosylated protein. Examples of samples which can be assayed via the methods of the present invention include, but are not limited to, individual cells and solutions including biological fluids such as serum.

According to the invention, the molecule that comprises the specific epitope to be detected is preferably detected using an epitope detector. In some embodiments, the epitope detector is an antibody, FAB, F(Ab)$_2$, Fv antibody fragment, CDR, CDR mimetic and engineered CDR structure linked to a nucleic acid molecule that serves as a RNA amplification template. In some embodiments, the epitope detector is a biotinylated antibody, FAb, F(Ab)$_2$, Fv antibody fragment, CDR, CDR mimetic and engineered CDR structure linked to a biotinylated nucleic acid molecule that serves as a RNA amplification template by a streptavidin bridge. In some embodiments, the epitope detector is a first antibody, FAb, F(Ab)$_2$, Fv antibody fragment, CDR, CDR mimetic and engineered CDR structure, which binds to the molecule that comprises the epitope, and a second antibody, FAb, F(Ab)$_2$, Fv antibody fragment, CDR, CDR mimetic and engineered CDR structure that binds to the first antibody, FAb, F(Ab)$_2$, Fv antibody fragment, CDR, CDR mimetic and engineered CDR structure and that is linked to a nucleic acid molecule that serves as a RNA amplification template. In some embodiments, the first antibody, FAb, F(Ab)$_2$, Fv antibody fragment, CDR, CDR mimetic and engineered CDR structure, which binds to the molecule that comprises the epitope, contains an epitope that is recognized by the second antibody, preferable a general or universal epitope. In preferred embodiments of the present invention, the general or universal epitope is a hemagglutinin HA tag or polyhistidine tag. An example of a general or universal epitope is a poly-His-tag such as those designed for the purification of the protein. In some embodiments, the second antibody, FAb, F(Ab)$_2$, Fv antibody fragment, CDR, CDR mimetic and engineered CDR structure that binds to the first antibody, FAb, F(Ab)$_2$, Fv antibody fragment, CDR, CDR mimetic and engineered CDR structure is biotinylated and is linked to a biotinylated nucleic acid molecule that serves as a RNA amplification template by a streptavidin bridge.

Antibodies are preferably monoclonal antibodies that bind to specific epitopes on a molecule. Such monoclonal antibodies can be made routinely. In some embodiments, antibodies are humanized or chimeric antibodies Alternatively, fragments of antibodies with the binding activity, scFv or CDR peptides can be used to replace antibodies in this technology. Fv fragments for selected epitopes can be produced in cells or on microorganisms by use of recombinant DNA technology. For example, Skerra and Pluckthun (Science 1988 240:1038-1044) describe an expression system for production of functional Fv fragments in *E. coli*.

A method for producing Fv fragments in eukaryotic host cells with a eukaryotic expression vector which has an operon having a DNA sequence which encodes the variable domain only of an antibody light or heavy chain has also been described (J. Mol. Biol. 1988 203:825-828). Chains of the Fv fragment are secreted and correctly assembled by the host cell such that fully functional Fv fragments are produced in the culture supernatant. In addition, the DNA coding sequence may be altered toward its 5' end so that the amino terminal end expresses a residue or residues with a surface suitable for covalent coupling of an oligonucleotide. In addition, the 3' terminal end may be varied so that cysteine residues are produced towards the C-terminal end of each variable domain permitting the variable domains in the dimer to become linked together by disulphide bonding. This may also promote assembly of the Fv fragment. Alternatively, the Fv fragment may be stabilized by use of a vector having a first DNA sequence encoding a first variable domain and a second DNA sequence encoding a second variable domain, the first and second sequences being linked by a third DNA sequence which encodes a joining peptide sequence. In this case, the joining peptide sequence is sufficiently long and flexible to allow folding of the two polypeptides into a functional single chain Fv. Preferably, the host cell is a myeloma cell line which, prior to transformation, does not secrete whole antibody or light chains. Such cells lines are well known and widely available (Reichmann et al. J. Mol. Biol. 1988 203: 825-828).

It is believed that random phage technology to any hapten or chemical compound can also be used to select Fvs. (Harrison et al. United States Biochemical Pharma. Ltd. (Europe), Watford, United Kingdom)

The CDR technology is well known and has been described in U.S. Pat. No. 5,334,702, U.S. Pat. No. 5,663,144, and U.S. Pat. No. 5,919,764, which are incorporated herein by reference. Antibody molecules bind to their antigens via six variable loops called Complementary Determining Regions (CDRs). The CDR3 from heavy chain often mediates that specificity. A general methodology for design of constrained cyclic CDR mimetics is described by Williams et al. (Proc. Natl. Acad. Sci. USA 1989 86:5537-5541), Sargovi et al. (Science 1991 253:792-795) and Murali et al. (Immunol. Res. 1998 17:163-169). In general, CDRs comprise a 6 to 15 mer peptide constrained to be cyclic and modified by aromatic residues. CDR mimetics are small molecules (about 1 kDa) which are capable of mimicking their parent antibodies in terms of specificity, affinity and biological activity. Cyclic forms of CDR mimetics contain approximately 5 to 13 constrained amino acids.

For purposes of the present invention, an epitope detector or epitope anchor comprising a CDR may consist essentially of the CDR or CDR mimetic. Alternatively, the epitope detector or epitope anchor may comprise a CDR or CDR mimetic defined as binding which is reinserted into a humanized antibody framework or attached to an Fc. CDRs or CDR mimetics reinserted into a humanized antibody framework or attached to an Fc. CDRs or CDR mimetics reinserted into a humanized antibody or attached to an Fc are also referred to herein as engineered CDR structures. However, as will be understood by those of skill in the art upon reading this disclosure, the term "engineered CDR structure" is inclusive of any protein into which a CDR or CDR mimetic is inserted. Examples of such proteins include, but are not limited to, members of the immunoglobulin gene family, minibodies or small antibody-like molecules, or any other framework which allows the CDR to be functional as an antigen binding surface.

An important step in the design of CDRs, CDR mimetics and engineered CDR structures for use in the present invention is the delineation of the residues that are important for activity. This is generally accomplished by first synthesizing a set of analogs from the bioactive domain of the original antibody or receptor or ligand of different lengths and establishing the minimal chain lengths for the complete and partial activities. Once the minimal chain length has been established, each side chain can be systematically varied to determine the importance of charge, steric bulk, hydrophobicity, aromaticity, and chirality at each position. After evaluation of the properties of a large set of analogs, it is possible to identify the functional groups and conformation features involved in binding. Different conformationally constrained analogs can then be developed. Various means for constraining peptides have been developed.

One means involves introducing a conformationally constrained amino acid. Hruby (Life Sci. 1982 31:189-199) describes the synthesis of a large number of amino acid and dipeptide derivatives with built-in conformational constraints, as well as their incorporation into biologically active peptides. Prasad et al. (Biopolymers 1995 35:11-20) also describes a method of constraining the conformation of an amino acid unit by replacing the hydrogen atom at the α-carbon with a methyl group to produce a dialkylamino acid. U.S. Pat. No. 6,022,523 describes a method that restricts the conformational freedom of amino acids by introducing a double-bond at the C-α and C-β atoms.

Another means for constraining peptides involves introduction of covalent cross-links. Constraining the peptide backbone by introduction of covalent cross-links provides more dramatic effects than incorporating unusual amino acids. Macrocyclization is often accomplished by forming an amide bond between the peptide N- and C-termini, between a side chain and the N or C terminus, or between two side chains. A head-to-tail cyclization of side protected peptides synthesized by Fmoc/t-butyl solid phase procedures on polysterine resin derivatized with 4-hydroxymethyl-3-methoxyphenoxyacetic acid, the first generation dialkoxy-benzyl linkage agent, has been described by Sheppard, R. C. (Int. J. Peptide Res. 1982 20:451-454). In addition, the analogous linkage agent, 4-(4-hydroxymethyl-3-methoxyphenoxy)-butyric acid (HAMA), was recently employed in fragment condensation and solid phase synthesis of peptides with these highly acid sensitive linkers (In Peptides, E. Giralt and D. Andreu eds, ESCOM, Leiden, The Netherlands 1991, 131-133). The enkephalin analogs described by Schiller provide an example of side-chain to backbone covalent cyclization in which covalent attachment of the e-amino group of the D-lys residue to the C terminal backbone carboxylate group of Leu produces a cyclic 16-membered ring analog with high potency and significant μ receptor selectivity (Schiller et al. Int. J. Pep. Prot. Res. 1985; 25:171-177). BOP-reagent and carbodimide/1-hydroxy-benzotriazole combinations have also been reported to be useful in the formation of cyclic peptides (Felix, A. M. Int. J. Pep. Prot. Res. 1988 31:231-238). Degrado et al. have also developed a biologically active cyclized peptide analog of the GP IIb/IIIa complex using m-aminomethylbenzoic acid as the linker (U.S. Pat. No. 6,022,523).

Disulphides can also be formed by oxidation via introduction of cysteine at certain positions. For example, Romani, S. (Int. J. Pep. Prot. Res. 1987 29:107-117) demonstrated that non-symmetrical disulphides can be built with the help of the di-tertbutyl aster of azodicarboxylic acid. Ploux, 0. (Int. J. Pep. Prot. Res. 1987 29:162-169) also describes a method for formation of non-symmetrical disulphides via thiol displacement of the 3S-3-nitro-2-pyridinesulfenyl group.

In a preferred embodiment, the oligonucleotide used in the present invention is double-stranded and comprises a T7 promoter driven cDNA sequence so that it can be amplified using T7 RNA polymerase. In this embodiment, double-stranded cDNA is synthesized for use as a template for T7 RNA polymerase transcription. T7 RNA polymerase requires its promoter site to be double-stranded. In a preferred embodiment, the oligonucleotide comprises a T7 promoter and a T7 terminator sequence.

In a preferred embodiment, the oligonucleotide is at least 50, preferably at least 100, more preferably at least 200, more preferably at least 300, more preferably at least 400, more preferably at least 500, and more preferably at least 600 base pairs in length.

In one embodiment, the site on the antibody, FAb, F(Ab)$_2$, Fv or CDR, CDR mimetic or engineered CDR structure to which the oligonucleotides are attached comprises a series of residues which allow the attachment of linkers consisting of chemicals such as heterodimeric coupling reagents or other linkers. These residues provide a uniform binding site for the linker attachment. The linkers attach to this site and also link oligonucleotides to the antibody, FAb, F(Ab)$_2$, Fv, CDR, CDR mimetic or engineered CDR structures. Oligonucleotides may be unmodified or modified. For example, the presence of the amplified oligonucleotide can be enhanced by incorporating a beacon or fluorescent labeled oligonucleotide into the mixture allowing for rapid semi quantitative assessment of the epitope expressing molecules (Ton et al. Chemistry 2000 6:1107-1111; Leone et al. Nucleic Acids Res. 1998 26(9):2150-2155).

In another embodiment, the oligonucleotide of the epitope detector is coupled to biotin and the monoclonal antibody, FAb, F(Ab)$_2$, humanized or chimeric antibody with or without a human Fc, single chain Fv or constrained epitope specific CDR, CDR mimetic or engineered CDR structure is coupled to streptavidin and attachment of the oligonucleotide to the monoclonal antibody, FAb, F(Ab)$_2$, humanized or chimeric antibody with or without a human Fc, single chain Fv or constrained epitope specific CDR, CDR mimetic or engineered CDR structures occurs via complexing of the biotin to the streptavidin. According to some embodiments, the oligonucleotide of the epitope detector is coupled to biotin and the monoclonal antibody, FAb, F(Ab)$_2$, humanized or chimeric antibody preferably with or without a human Fc, single chain Fv or constrained epitope specific CDR, CDR mimetic or engineered CDR structure is coupled to biotin and the oligonucleotide and monoclonal antibody, FAb, F(Ab)$_2$, humanized or chimeric antibody preferably with or without a human Fc, single chain Fv or constrained epitope specific CDR, CDR mimetic or engineered CDR structure are linked to each other through the interaction of each biotin to streptavidin thereby attaching the oligonucleotide to the monoclonal antibody, FAb, F(Ab)$_2$, humanized or chimeric antibody preferably with or without a human Fc, single chain Fv or constrained epitope specific CDR, CDR mimetic or engineered CDR structures.

In some embodiments, oligonucleotides are biotinylated on both the 5' and 3' end so that, when contacted with streptavidin, two or more oligonucleotides may be bound to each other in addition to binding to the epitope detector.

Bound epitope detectors may be quantified by methods such as amplification by conventional PCR or aRNA techniques. If the detection method used is immuno aRNA, double-stranded cDNA are preferably used in the epitope detector. In this embodiment, aRNA is transcribed on the solid support using a polymerase, unlabeled ribonucleotides, and fluorescently labeled ribonucleotides. By "polymerase" for purposes of the present invention, it is meant a polymerase which recognizes a specific promoter. Examples of polymerases useful in the present invention include, but are not limited to, T7 RNA polymerase, T3 RNA polymerase, SP6 RNA polymerase, 29 polymerase, and Taq polymerase. In another embodiment, the amplified products can serve as templates for further amplification with reverse transcriptase or replicases to increase the sensitivity.

Molecules that bind to the selected epitope are non-covalently bound to the oligonucleotide. In some embodiments, the biotinylated molecule that binds to the selected epitope may be added simultaneously with the streptavidin, and biotinylated oligonucleotide. In some embodiments, the reagents are premixed. In some embodiments the reagents are added sequentially. In some embodiments, streptavidin and biotinylated oligonucleotides are added repeatedly to enhance signals. In some embodiments, an excess of streptavidin and biotinylated oligonucleotides are provided in sufficient amounts to link more than one biotinylated oligonucleotide per biotinylated molecule that binds to a selected epitope, thereby enhancing the signal.

A variety of means are available for detection of amplified products of the epitope detector. In one embodiment, the nucleic acid sequence is detectably labeled such as with a radioactive label or a fluorescent label. In a preferred embodiment, the nucleic acid sequence is not labeled but rather is stained by fluorescent dye. Other methods such as gel electrophoresis, high performance liquid chromatography, hybridization assays, immunohistochemical assays and/or specific binding protein assays can also be used for detection. In addition, concentration of RNA amplification product may be measured by hybridization with sequence-specific probes. Such probes can be fluorescent oligos or molecular beacons based on fluorescence resonance energy transfer (FRET).

The method of the present invention has widespread applicability in both medicinal and research purposes.

A preferred means for detection in the present invention comprises staining with a fluorescent dye. In this embodiment, after RNA amplification with a polymerase such as T7 RNA polymerase, T3 RNA polymerase, SP6 RNA polymerase, 29 polymerase or Taq polymerase, a portion of the reaction mixture can be mixed with a fluorescent dye such as RiboGreen reagent (Molecular Probes, Inc) (U.S. Pat. No. 5,436,134), a unsymmetrical cyanine dye that binds to RNA directly in the solution and then releases fluorescence signals. Examples of other fluorescent dyes with similar properties useful in this method include, but are not limited to, PicoGreen, TOTO-1 or YOYO-1. The reactions are preferably performed in microplates and the fluorescence is read using a fluorimeter such as the Spectra Fluora 5 to 15 minutes after mixing RNA solutions with RiboGreen dye. The fluorescent reading may be collected at 535 nm.

In some methods of the present invention, a mixture of epitope detectors comprising either monoclonal antibodies to selected epitopes, FAb to selected epitopes, F(Ab)$_2$ to selected epitopes, humanized or chimeric antibody to selected epitopes, single chain Fvs for selected epitopes, or constrained epitope specific CDRs, CDR mimetics or engineered CDR structures, conjugated with oligonucleotides of different lengths can be used in a single reaction to probe the cell lysate to provide a profile of proteins in the cell lysate via automatic sequencing. In this method, after amplification and staining of the amplified products with a fluorescent dye, the reaction mixture is separated by electrophoresis and the size of the RNA products are visualized by fluorescent dyes or probes. Moreover, different oligonucleotides linked to different molecules specific for different epitopes may be provided with different sequences such that specific probes can hybridize with the reaction mixture and reveal the presence and abundance of the corresponding antigens.

Using a biotinylated detection antibody (or antibody fragments, CDR, phage antibodies) that are non-covalently linked to biotinylated oligonucleotides, the methods of the invention can detect any kinds of antigens that are recognized by antibodies, including but not limited to proteins, post-translational modification (phosphorylation, ubiquitinylation, etc), carbohydrates, etc. Alternatively, the methods can be used to detect interaction partners by using biotinylated proteins, peptides, organic structures, etc. By using biotinylated vs un-labeled molecules, the methods can also be applied to competitive binding assay for the quantification of target molecules.

The present invention provides a sensitive detection method which eliminates concerns about the non-quantitative nature of immuno-PCR techniques and which offers vast potential in the field of proteomics. By using a polymerase which recognizes a specific promoter such as T7 RNA polymerase, T3 RNA polymerase, SP6 RNA polymerase, 29 polymerase or Taq polymerase as well as the specific promoter in the amplification step, assays performed in accordance with this method possess linear amplification and precise quantification which are relevant to biological and medical assays. The number of factors that affect the sensitivity of detection have also been reduced. The specific binding between antigens and their antibody, FAb, F(Ab)$_2$, Fv or monovalent CDR, CDR mimetic or engineered CDR structure is the only critical parameter of this method.

The ability to provide universal epitope detectors provides the method of the present invention with multiple additional advantages. First, any cellular antigens can be detected without having been first coupled to a monoclonal antibody with ds-oligo. Without the universal probe, the method would only be useful in looking at one or several particular antigens at a time. The universal probe, on the other hand, allows for the detection of any cellular or fluid residing antigen with available antibodies, FAb, F(Ab)$_2$, Fvs, CDRs, CDR mimetics or engineered CDR structures. In addition, with slight modification in the protocol, different proteins can be detected simultaneously in a single electrophoresis lane when oligonucleotides of different sizes are attached to the antibody, FAb, F(Ab)$_2$, Fv, CDR, CDR mimetic or engineered CDR structure of the epitope detector. Thus, as demonstrated herein, the method of the present invention provides a versatile technique that is applicable in the identification of protein antigens as well as post-translational modification of polypeptides and other structures such as sugars or lipids at the single cell level of detection.

Likewise, the use of streptavidin bridges allows for the easy adaptation of existing antibodies, FAb, F(Ab)$_2$, Fvs, CDRs, CDR mimetics or engineered CDR structures to be used in methods of the present invention. Such antibodies, FAb, F(Ab)$_2$, Fvs, CDRs, CDR mimetics or engineered CDR structures can be biotinylated and used in the present invention. The ease of adapting existing antibodies, FAb, F(Ab)$_2$, Fvs, CDRs, CDR mimetics or engineered CDR structures for use in the present invention makes the present invention particularly advantageous over other methods.

The method of the present invention is also useful in the analysis of interactions of molecules and the detection of small molecules. For example, epitope specific molecules can be used as epitope detectors on tissue samples to identify the expression of specific receptors, or vice verse. With available antibodies, FAb, F(Ab)$_2$, Fvs, CDRs, CDR mimetics or engineered CDR structures, or binding proteins, small molecules such as toxins or drug metabolites, can be detected in any solution including, but not limited to, water, foods, and body fluids.

To study the interactions of molecules, a two-component (molecule A/molecule B) interaction system is developed. The two components, molecule A and molecule B may comprise proteins, sugars, or other types of chemical entities including, but not limited to, carbohydrates, DNA or RNA, or peptides with structural conformations such as alpha helices or beta-sheets. To develop this two-component system, an epitope detector such as an antibody for a first molecule, referred to hereafter as molecule A, is placed in proximity with a sample comprising molecule A so that molecule A binds to the epitope detector. A solution containing products of an expression library constructed so that each expressed protein also contains a HA tag or similar tag can then be added to identify molecules which interact with molecule A. For purposes of the present invention, these molecules are referred to herein as molecule B or a second molecule. Alternatively, normal cellular extracts or lysates or any fluid containing potential molecule B can be used.

If the second molecule, molecule B, in the library product or cellular extract or lysate binds to the first molecule A bound by the epitope detector, the new molecules can be detected with either a universal detector that binds to the tag or marker or by the use of a CDR library or a scFv library specific against molecule B. In a preferred embodiment, monitoring of the interaction between molecule A and molecule B is performed by the fluorescence based quantifiable assay which detects the amplified nucleic acid sequence from the oligonucleotide conjugated to the universal detector.

When one of the molecules of the two-component (molecule A/molecule B) interaction system binds a ligand or pharmaceutical drug, the two-component system can be used to investigate the effects of the ligand or drug on the binding of molecule A to molecule B. Accordingly, the present invention also provides an in vitro system for monitoring drug affects on interactions of molecules. The ligand or drug can be added at any step in the assay to determine how the ligand or pharmaceutical drug alters the binding of molecule A to molecule B. In addition, more than one drug can be added to the two-component interaction system. For example, a second drug such as an antagonist of the first drug can be added and the level of binding of A to B as well as to the complex of A and B can be determined. Further, instead of known ligands or drugs, a third solution containing the products of another library of molecule C marked with other tags could be added to the complex of A and B and the effects of this third solution on binding can be determined.

Thus, the present invention provides a rapid in vitro screening assay with a biological readout, namely the formation of a complex interaction. Further, using this type of system it is possible to build screening systems that act like organic analogue computers whose output is dependent on the number of events developed with each progressive addition. These progressive events are disturbed upon addition of a third molecule such as a pharmaceutical drug or ligand that interferes with this assembly. The quantification of signals before and after addition of the third molecule defines the change in output. A positive change means that the pharmaceutical drug or ligand facilitates the binding of molecule A to molecule B, while a negative change means that the pharmaceutical drug or ligand inhibits the binding of molecule A to molecule B.

The present invention can also be used to identify active CDRs, CDR mimetics or engineered CDR structures and study via the present invention families of proteins associated with a particular disease state, i.e the erbB family and it association with origin and early detection of malignancy. For example, a library has been developed containing a large and diverse population of CDR mimetics (>106) of a single ring size that develop into constrained turns and also possess aromatically modified termini. This particular library was produced using the M13 phage system and contains a large repertoire of CDR-streptavidin binding moieties diversified from a 6 membered AHNP peptide through randomization. For diversification of the library, the synthesized oligonucleotide library encoding randomized CDR regions, but with a fixed constrained framework region, are inserted into the phage construct that leads to the expression of the highly varied CDR streptavidin fusion proteins.

CDR-SA libraries can be used in the present invention, for example, to screen transformed cell lines and tumor cells for tumor surface markers. In this embodiment, initial screening preferably employs fluorescence based microfluorimetry for binding to cells followed by an ELISA type assay for binding to captured proteins derived from cell lysates. For example, a monoclonal antibody can be attached to P13-kinase or ras and any bound CDR-SA forms can be detected. The sequence of any unknown targets of tumor specific selected CDR-SA molecules can then be determined. In one embodiment, purified CDR-SA is used to screen a cDNA expression library constructed in cells such as COS7 cells and in expression libraries prepared from freshly isolated tumor tissues from various stages of malignancy.

Libraries of CDRs, CDR mimetics or engineered CDR structures can also be used to generate a spectrum of probes to detect receptors, proteins associated upon activation of the receptors and proteins involved in pathways associated with the receptors. For example, a CDR mimetic library can be used to generate a spectrum of probes to erbB receptors, proteins associated upon activation of erbB receptors and proteins involved in pathways associated with erbB receptors such as the PI-3 kinase pathway.

CDRs or CDR mimetics of libraries defined as binding to a receptor, proteins associated upon activation of a receptor or proteins involved in pathways associated with the receptor are can also be used therapeutically to target the receptor or protein. In a preferred embodiment for therapeutic use, the CDR or CDR mimetic is reinserted into a humanized antibody framework or attached to an Fc. In this embodiment, the engineered CDR structure may be administered alone or may further comprise a radiolabel or cytotoxin attached thereto.

Methods for preparing scFY libraries with some randomly changed CDRs are described by winter et al. in U.S. Pat. No. 6,291,650, U.S. Pat. No. 6,225,447, U.S. Pat. No. 6,172,197 and U.S. Pat. No. 6,140,471. However, production of CDR-SA libraries is not described by Winter et al.

Also provided in the present invention are kits for performing the methods of the present invention. In one embodiment, a kit is provided for the detection of molecules expressing a selected epitope. In a preferred embodiment, detection of the molecule is performed via a fluorescent dye that stains nucleic acid sequences. In some embodiments, the kit comprises a container that contains an oligonucleotide, preferably one at least 100, more preferably at least 200, more preferably at least 300, more preferably at least 400, more preferably at least 500, more preferably at least 600 base pairs. The oligonucleotide comprises an RNA polymerase promoter and preferably an RNA polymerase termination sequence. In some preferred embodiments the oligonucleotide comprises a T7 promoter. In some preferred embodiments the oligonucleotide comprises a T7 promoter and a T7 termination sequence. The oligonucleotide is preferably biotinylated. The kit may optionally provide reagents for biotinylating the oligonucleotide. In some embodiments, the kit provides streptavidin or avidin. In some embodiments, the kit provides a molecule that specifically binds to an epitope such as antibodies, FAb, F(Ab)$_2$, Fvs, CDRs, CDR mimetics or engineered CDR structures. In some embodiments the antibodies, FAb, F(Ab)$_2$, Fvs, CDRs, CDR mimetics or engineered CDR structures are biotinylated. In some embodiments the kit provides reagents for biotinylating the antibodies, FAb, F(Ab)$_2$, Fvs, CDRs, CDR mimetics or engineered CDR structures. In some embodiments, the molecules that bind to the epitope comprise a universal epitope that binds with antibodies, FAb, F(Ab)$_2$, Fvs, CDRs, CDR mimetics or engineered CDR structures. Such antibodies, FAb, F(Ab)$_2$, Fvs, CDRs, CDR mimetics or engineered CDR structures may be biotinylated. Kits may also provide a container that contains an RNA polymerase and/or a container that contains an amplification reaction buffer and/or a container that contains an RNA polymerase and a fluorescent dye. The RNA polymerase is preferably T7 polymerase.

In another embodiment, kits are provided for profiling proteins in a mixture such as a cell lysate. In this embodiment, the kit preferably comprises a mixture of epitope detectors comprising monoclonal antibodies for selected epitopes, FAbs for selected epitopes, F(Ab)$_2$s for selected epitopes, humanized or chimeric antibody for selected epitope, single chain Fvs for selected epitopes or constrained epitope specific CDRs. The epitope detectors are preferably biotinylated or the kit provides reagents for biotinylating them. The kits provide multiple different oligonucleotides, each having a different length. The lengths vary and are from preferably one at least 100, more preferably at least 200, more preferably at least 300, more preferably at least 400, more preferably at least 500, more preferably at least 600 base pairs. The oligonucleotides comprise an RNA polymerase promoter and preferably an RNA polymerase termination sequence. In some preferred embodiments the oligonucleotides comprise a T7 promoter. In some preferred embodiments the oligonucleotides comprise a T7 promoter and a T7 termination sequence. The oligonucleotides are preferably biotinylated. The kit may optionally provide reagents for biotinylating the oligonucleotides. The kits may contain size markers corresponding the to sizes of the various oligonucleotides which can be used to identify which oligonucleotides have been amplified. Kits may also optionally contain streptavidin or avidin and/or an RNA polymerase and/or an amplification reaction buffer and/or a fluorescent dye.

The original immuno-PCR used pure antigens in the assay. Later iterations of immuno-PCR examined mixed antigens (Hendrickson et al. Nucleic Acids Research 1999 23(3):522-529) but only showed sensitivity of two to three orders of magnitude higher than ELISA. In a real-world assay with the background comprising a huge variety of non-specific antigens, sensitivity is always limited by the specificity of the assay. Epitopes bound by the antibodies, FAbs, F(Ab)$_2$s, Fvs or CDR fragments are expected to identify larger polypeptides and can be used to identify motifs in supernatants, fluids, extracts of cells or bacteria or any other eukaryotic organism. Further, actual identity of the polypeptides, organic molecules or sugar structures can be determined by computer aided analysis of data bases using the binding of several epitopes by Fvs as a guide. For example, binding by Fv a, d, e, and f would identify a sugar molecule as having side chains a, d, e, and f, and hence belonging to a family of sugars having these same side chains. In this way the present invention allows definition and identification of many, if not all molecules in a cell at any one particular time. Moreover this approach can be used to identify alternative transcriptional forms translated in an active cell or cellular supernatant. This procedure is easily amenable to 1) use with nonradioactive detection methods, most preferably fluorescent dyes 2) microtized liquid handling procedures, 3) low sample volume detection such as "protein chip" analysis and 4) robotization. For example, a chip can be developed which contains multiple binding elements or units and a single universal epitope detector. A binding element that recognizes a common surface on the monoclonal antibody, the FAb, the F(Ab)$_2$, the humanized or chimeric antibody, the single chain Fv, or the CDR, CDR mimetic or engineered CDR structure, such as a universal antibody can be used. Alternatively, avidin can by built into each antibody, single chain Fv or CDR, CDR mimetic or engineered CDR structure and biotin can be coupled to the oligonucleotide. These chips provide the advantage of more rapid and higher affinity thereby multiplying the signal.

The following nonlimiting example is provided to further illustrate the present invention.

EXAMPLE

A novel detection procedure that is isothermal and allows linear quantification and facile industrial adoption is described herein. The procedure uses streptavidin to bridge the double stranded template to the detection antibody. A fluorescent RNA intercalating dye (RiboGreen, Molecular Probes) is used to quantify the yield of amplified RNA and thus eliminates the use of radioactivity as well as tedious electrophoresis. all reactions can be performed in 96- or 384-well plates. The new approach may be referred to as the Fluorescent Amplification Catalyzed by T7 polymerase Technique (FACTT) and used to analyze low abundance proteins in serum and provide comparisons to the widely practiced ELISA technology.

The fluorescence of the intercalating dye RiboGreen increases more than 1000 fold upon binding to RNA fragments but is not enhanced by the presence of free nucleotides. With a detection limit of 1 ng/ml RNA in solution, Ribogreen is 200-fold more sensitive than ethidium bromide-based assays. Ribogreen usage is optimized in the present methodology. Earlier uses of Ribogreen failed to generate substantial fluorescent readouts from the short ds-oligo (50-60 bp) template. A longer RNA strand was developed that offered a greater surface to interact with dye and was found to generate stronger signals. For this reason, a new ds-DNA template (D2) of about 600 bp by PCR is used. To facilitate binding to streptavidin, biotinylation was introduced to the ds-DNA simply by using a biotinylated 5' PCR primer. D2 contains a T7 promoter sequence at the 5' end and a T7 terminator sequence at the 3' end. The D2 template provides better T7 amplification efficiency compared with a control ds-DNA missing the 3' T7 terminator sequence, suggesting that T7 terminator sequence improves the transcription efficiency of T7 RNA polymerase for linear template. The D2 template coupled to biotin may be termed the amplification module (AM).

The AM binds to streptavidin that has interacted with biotinylated antibody. Streptavidin is tetravalent, and the biotinylated AM therefore could be bridged to the detection antibody via streptavidin (see FIG. 1). To test if the amplification module was in fact able to bind streptavidin, streptavidin ranging from 5 μg/ml to as low as 0.5 fg/ml was immobilized directly to 384-well plates and used in a simplified FACTT assay.

Figure 2:
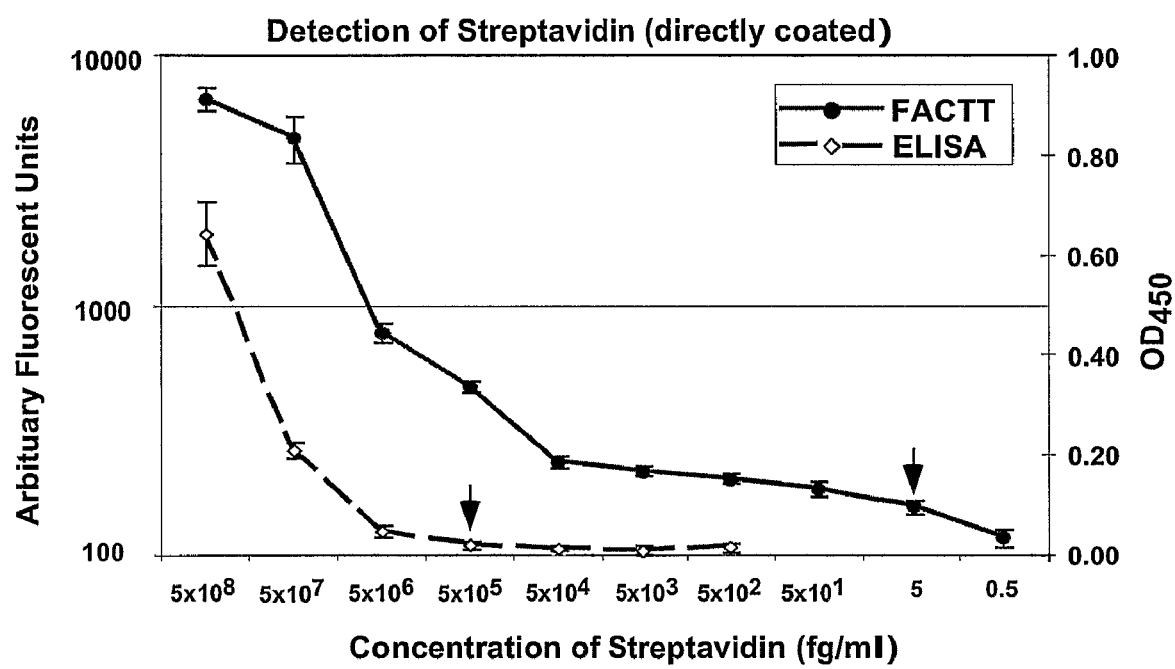
FIG. 2 provides data from experiments comparing detection of streptavidin using an embodiment of the present invention (FACTT) and (ELISA). Streptavidin was pre-coated to a 384-well (FACTT) or 96-well plate (ELISA) at different concentrations as indicated. To detect streptavidin, Biotin-DNA was used in FACTT (left axis) while biotin-HRP was used in ELISA (right axis). Values are presented as the average of three independent experiments. bars, SE.

After the amplification module was incubated with streptavidin for one hour, the unbound module was removed and the plated was washed six times with PBST. T7 RNA polymerase was added directly into 384 wells along with reaction buffer and NTP mixtures. As shown in FIG. 2, streptavidin, ranging from 5 μg/ml to as low as 0.5 pg/ml, was successfully detected in a dose-dependent manner over 9 orders of magnitude dynamic range. All readings from streptavidin samples were significantly different from the control by statistical calculations. The slope of the FACTT curve is less than 1. In fact, the slope of the FACTT curve changed. When the T7 RNA polymerase-directed reaction was tested using the DNA template, a 10-fold increase in the template concentration only led to about a 2-fold rise in fluorescent readings. This characteristic of the amplification makes it possible for FACTT to produce dose-dependent readings over a wide range of concentrations.

To compare generic FACTT with ELISA, we set up an ELISA assay in parallel, in which biotinylated HRP was used to detect the coated streptavidin. As expected, when 3 SD over background was used as the cut-off, only streptavidin samples with concentrations over 5 ng/ml were able to show statistical significant difference than the control. The data suggest that generically FACTT is at least 105 fold more sensitive than ELISA is.

Assuming that all streptavidin molecules in each well in FIG. 2 are immobilized to plates and remain active, the lowest detectable concentration (5 fg/ml or 0.6 fM) correspond to $1.2 \times 10^{-21}$ molar of tetrameric streptavidin in the well, or about 700 molecules. In a typical FACTT reaction, the antigen of interest can be immobilized to a certain extent depending on the affinity of the capture antibody. Each detection antibody has more than one available biotin site, suggesting the real detection limit of the number of antigens is even lower.

Figure 3:
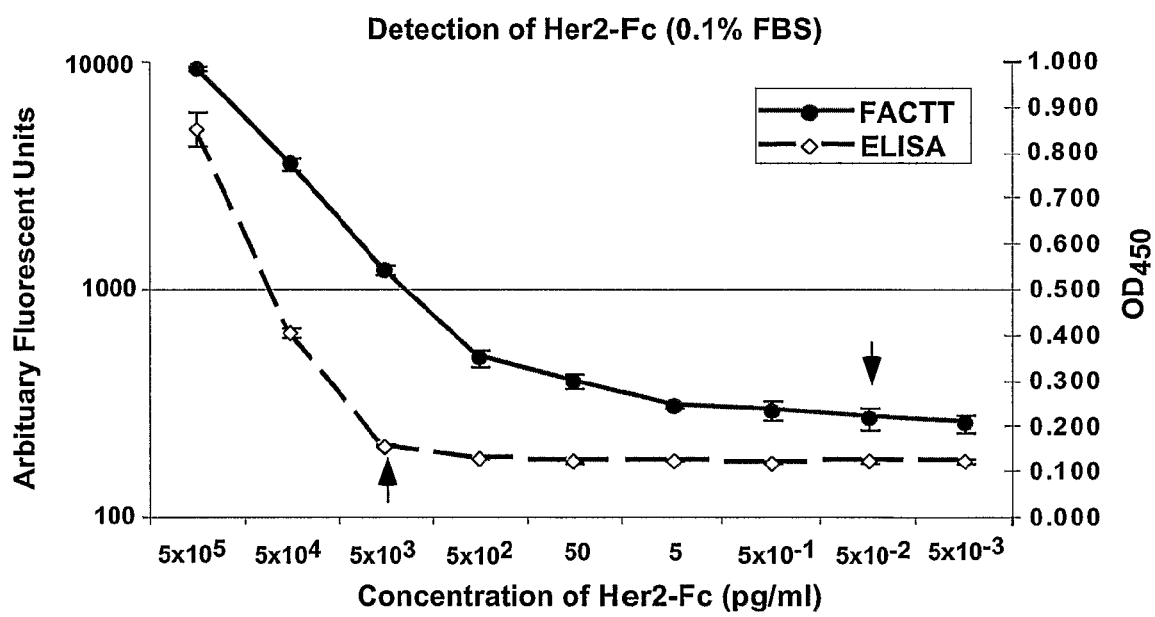
FIG. 3 contains data from experiments comparing detection of p185her2 using an embodiment of the present invention (FACTT) and (ELISA). The extracellular domain of p185her2, which contains the epitope for mAb 4D5, was expressed as an Fc-fusion protein and designated as Her2-Fc. 1E1, which recognizes an epitope different from that of 4D5, was coated on a 384-well plate at 5 μg/ml and 20 μl/well. A serial dilution of Her2-Fc in 0.1% serum, from $5 \times 10^5$ to $5 \times 10^{-2}$ pg/ml, was added to the coated plate at 20 μl/well. 20 μl of diluted biotinylated 4D5 (180 ng/ml) was used for each well. Streptavidin and biotinylated DNA templates (AM) were added sequentially at 5 μg/ml and 250 ng/ml respectively. By, FACTT (left axis), Her2-Fc can be detected at a concentration as low as 5 pg/ml (7.5 femtograms/well) with statistically significant difference versus control by Student's t Test (<0.05) Relative fluorescent intensity was determined as the fluorescent reading of each sample relative to that of control. Values are presented as the average of three independent experiments. bars. A control ELISA experiment is also included (right axis).

To extend this set of studies, the Receptor Tyrosine Kinase p185her2/neu, a therapeutic and diagnostic target overexpressed in more than 30% of primary breast, ovarian and pancreatic tumors was chosen. Specifically, the recombinant Her2-Fc fusion protein was used as the antigen and 4D5 as the biotinylated detection antibody. Her2-Fc was subjected to a serial of 10-fold dilution in PBS containing 0.1% FBS and presented to the capture mAb (anchor) 1E1. 1E1 and the biotinylated detection antibody h4D5 bind to distinct epitopes on the extracellular domain of the p185her2/neu receptor. After biotinylated 4D5 was added to the plate to bind the captured antigen, streptavidin and the amplification module were added sequentially. Non-bound molecules were then washed way, and T7 RNA polymerase was used to amplify the amplification module that was associated with the antibody-antigen-antibody complex. A representative study of binding and detection of Her2-Fc indicated that this technology allowed very sensitive detection of Her2-Fc protein (FIG. 3). From 0.5 μg/ml to as low as 0.05 pg/ml (about 0.5 fM) of Her2-Fc, FACTT produced dose-dependent fluorescent signals with readings significantly different from the control ($P<0.05$) and higher than the control by 3 SD. In a control ELISA assay using the same pair of p185her2/neu specific antibodies and the HRP-anti-human IgG as the secondary antibody, the detection limit is 5 ng/ml (FIG. 3). This sensitivity of FACTT is again 5 orders of magnitude more sensitive and specific than that of ELISA.

Figure 4:
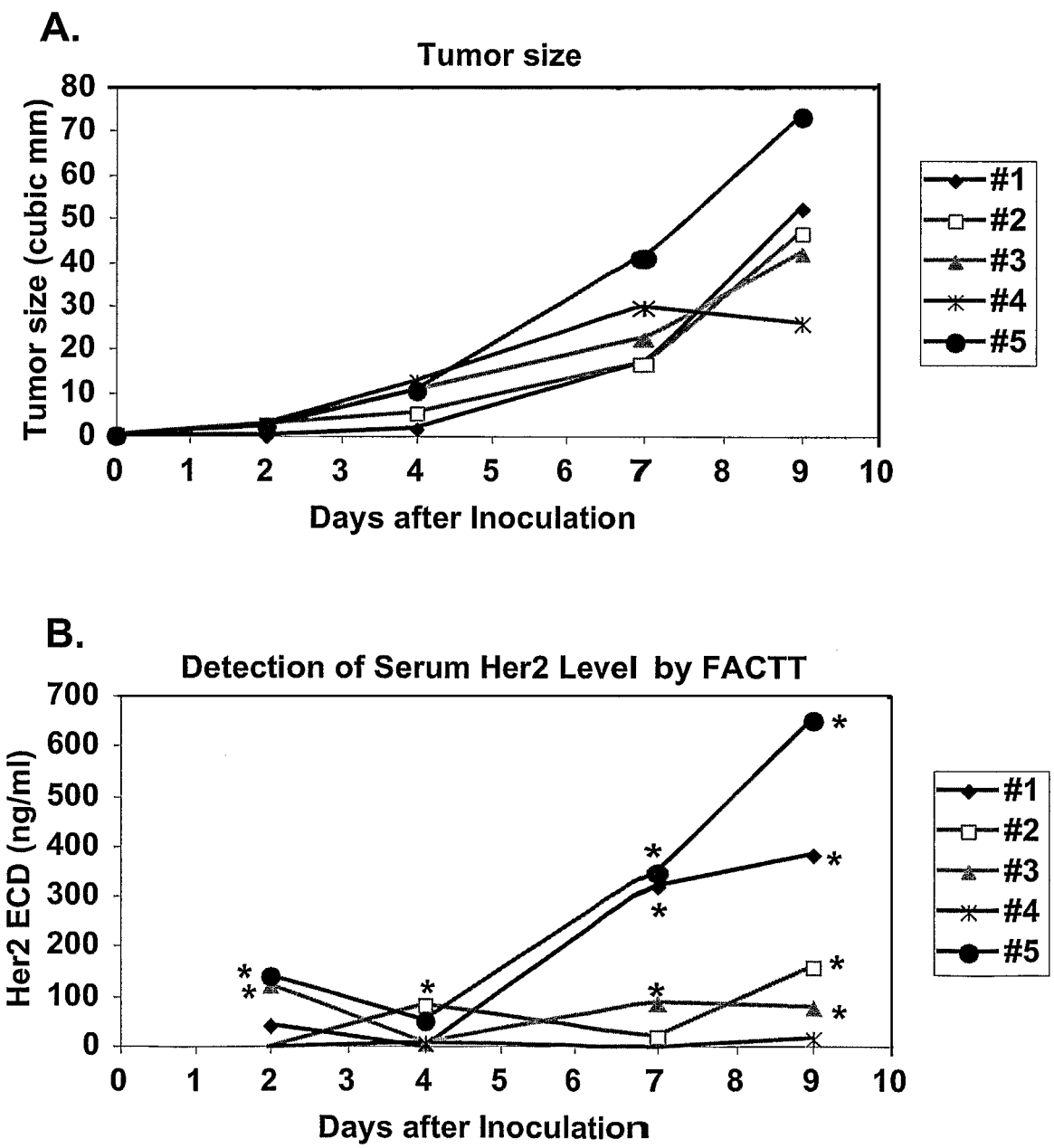
FIG. 4, panels A and B: Detection of serum Her2. A similar FACTT assay as described in FIG. 3 was performed with serum samples collected at the indicated time. On day 0, $10^6$ Her2-expressing T6-17 cells were subcutaneously inoculated into the dorsal flank of each mouse. Panel A. The size of visible tumors was measured at the time when serum samples were collected. Panel B. Serum Her2 concentration detected by FACTT. Mouse sera were diluted by 1:50 in PBS and 20 μl of the diluted sample was used for each FACTT test. Samples higher than the baseline ("0", the normal mouse serum) by 3 SD were indicated by "*".

The ectodomain of Her2, which is shed from the cell surface, has been detected in the sera of breast cancer patients. Higher serum concentration of Her2 correlates with lower response rate to hormone/chemotherapy and shorter survival time after relapse. Here in a time-course study FACTT was performed to test if Her2 can be detected in the serum from nude mice carrying tumors driven solely by over expressed but non-mutated Her2/neu. FIG. 4 shows data collected from a group of 5 animals. The size of tumors was measured manually (FIG. 4 Panel A) and serum samples were collected at day 2, 4, 7 and 9 after inoculation. Her2 levels in the serum was detected by FACTT using a commercial Her2 ECD standard (Oncogene Sciences) and presented as relative concentrations over control normal serum (FIG. 4, Panel B). Generally the trend of the increase of serum Her2 level correlated with the growth of tumors. A plot of all calculated serum Her2 concentrations against their corresponding tumor sizes showed a correlation coefficient of 0.55 ($p<0.01$), indicating a reasonable correlation between the serum Her2 levels and the tumor sizes. There was a better correlation when the tumor is larger than 10 mm$^3$. At day 9 after inoculation all mice except #4, which had the smallest tumor, had elevated serum Her2 levels (>3 SD over basal levels). Notably the use of ELISA could not detect Her2/neu in the serum even at day 11. These data support detection of very early tumor masses by using FACTT on serum samples.

Figure 5:
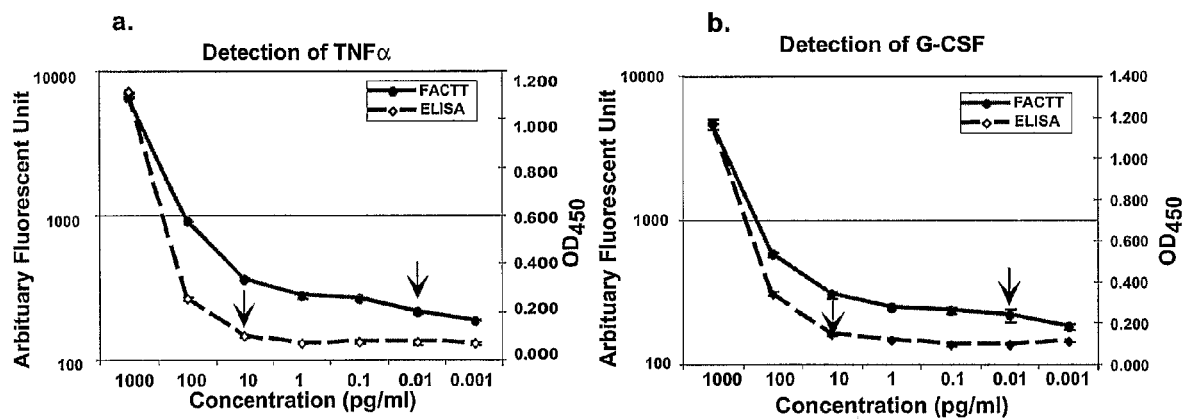
FIG. 5, Panels a and b: Detection of TNFα and G-CSF by FACTT. Serial dilutions of TNFα (Panel a) and G-CSF (Panel b) were detected by FACTT (solid line, left axis) or ELISA (dashed line, right axis) using DuoSet antibodies from R&D Systems. The arrows point to the limits of detection in each assay.

To demonstrate that FACTT is a general approach, FACTT was used to detect TNFα and G-CSF, two cytokines that were studied previously by immuno-Rolling-circle amplification (RCA). In a control ELISA assay, both TNFα and G-CSF had a detection limit of 10 pg/ml (FIG. 5). In the immuno-RCA study, the detection limit for TNFα was comparable to ELISA (10 pg/ml) while the sensitivity for G-CSF was much lower (1000 pg/ml). In our FACTT assay, the detection limit for both TNFα and G-CSF is 0.01 pg/ml, a sensitivity that is 3 orders of magnitude higher than ELISA or immuno-RCA (FIG. 5).

In addition to streptavidin and Her2-Fc, recombinant prion protein in sera has also detected by FACTT. All proteins have been detected with a sensitivity of about $10^4$ fold higher than by ELISA. In addition, dose-dependent signals can be observed over a much broader range of target concentrations. The increased sensitivity and broader range may be attributed to the linear production of RNA molecules by T7 RNA polymerase, which consistently progresses through the template with a transcription rate of 97-115 nucleotides per second. Combining the amplification module and the non-covalent streptavidin interaction is critical to provide the sensitivity and reproducibility to this approach.

There are several approaches for fluorescent detection of amplified RNA. In this report, the intercalating dye, RiboGreen was used. RiboGreen may not be the most sensitive way to analyze RNA concentration, but it simplifies FACTT assays to perform in the 384-well plate format. In addition, RiboGreen detection only requires 5-10 minutes to determine the amount of amplified RNA using a standard fluorimeter. Although FACTT was performed manually, the current format is absolutely compatible with the available high-throughput robotic sample handling. The easy automation of the FACTT approach is expected in the future when studying multiple antigens.

FACTT can be further optimized by using different antibody conjugates or detection reagents. For example, sensitivity of FACTT can potentially increase several orders of magnitude with antibodies linked to high-density DNA nanoparticles. In addition, recombinant antibodies produced from phage libraries can also provide a large repertories of reagents to facilitate the FACTT detection.

The most widely used clinical Her2 tests are IHC (immunohistochemistry) and FISH (fluorescence in situ hybridization). IHC measures the Her2 protein expression level while FISH detects the amplified gene copy numbers. Patients tested as FISH positive or IHC positive (Grade 3+) have comparable responsive rate (34~35%) to Herceptin therapy. However, in many cases there is high disconcordance between IHC and FISH results. Loss of protein antigens in fixed tissue slides and subjective observations during the IHC procedure (IHC−, FISH+) as well as protein overexpression without gene amplification (IHC+, FISH−) account for such a discrepancy.

Her2 can also be detected from the serum of breast cancer patients. Pre-treatment serum Her2 levels positively correlated with tumor size, number of invaded lymph nodes, and histological scores. In another study, the serum Her2 level was a better indicator for Stage 1V breast cancer than IHC scores. Post-treatment serum Her2 level was also of prognostic value for metastasis-free survival and disease-specific survival. A clinical ELISA assay for serum Her2 has also been developed. This assay requires a special machine. In this assay, the cut-off level to differentiate positive and negative samples is 15 ng/ml, a level very close to the detection limit of ELISA.

With far greater sensitivity than the ELISA assay and with adaptability to high-throughput techniques, FACTT can substitute ELISA for clinical detection of low abundance antigens. Current detection assays for many clinical targets, such as pathogens and diagnostic proteins (e.g. *Helicobacter pylori*, leptin, insulin and c-Peptide) have been established already in ELISA formats. In many cases the detection antibody is also biotinylated. Simple adaptation of FACTT with the available ELISA reagents (antibody pairs) will make it possible to detect antigens from less clinical samples or monitor antigen levels at an earlier stage.

FACTT can also be applied to antibody arrays. Currently several ELISA-based antibody arrays have been developed for cytokine detections and characterizing phosphorylation of signal proteins. With greater sensitivity than ELISA, FACTT can enhance these arrays. FACTT will be also useful in analyzing fractional cell populations that are affinity isolated and studied for specific biochemical characteristics. Cell numbers for such populations are generally low and will be undetectable by other less sensitive methods.

Finally FACTT can also be used as an alternative approach for Proteomics, which is currently highly dependent on 2D electrophoresis-Mass Spectrometry (2D-MS). In addition to its bias for abundant proteins, 2D-MS is also generally unsuccessful in identifying hydrophobic proteins and proteins with low or high molecular weight, as well as protein post-translational modifications. The application of FACTT to diagnostic areas will help in improving our biochemical understanding of normal and abnormal proteins, carbohydrates, and lipids involved in health and disease.

Material and Methods

Antibodies:
Anti-p185her2/neu antibody 1E1, 6E2 and A18 were developed with a human p185her2/neu expression cell line T6-17. Humanized 4D5 (h4D5, a.k.a. Herceptin) was graciously provided by Genentech. 1E1/biotinylated 4D5 set was used to detect Her2-Fc, while 6E2/biotinylated A18 set was used to detect serum Her2 since the commercial Her2 ECD standard (Oncogene Sciences) was not recognized by 1E1/biotinylated 4D5. Antibodies to TNFα and G-CSF (DuoSet ELISA development system) were purchased from R&D Systems.

DNA Constructs:
The plasmid pTD2T was constructed by subcloning the EcoRI/Aat II (blunted) fragment of pCal-n-EK D2, which contained the Domain II of Her2 and the T7 terminator, into the EcoRI/EcoRV sites of a pcDNA vector pHA2. To prepare the biotin-DNA template for IDAT, a biotinylated upstream primer (Biotin5', seq: 5'ggctaactagagaacccact3') and a downstream primer (T7terR, seq: 5' ttggttatgccggtact3') were used with pTD2T in a PCR reaction. Alternatively, reverse primer GST2r (5'ccgctcgagtcaggcacagggcttgctgcacttc3'), which was located at the 5' of the T7 terminator, was used with Biotin 5' in the PCR to generate the control template D2X. All primers were synthesized by the Nucleic Acid Facility of Department of Chemistry of the University of Pennsylvania.

Biotinylation of Antibodies:
h4D5 was directly biotinylated using the EZ-link sulfo-NHS-LC-Biotin from Pierce. Briefly, h4D5 (0.25 mg/ml, 100 µl) was mixed with Sulfo-NHS-LC-Biotin (1 mg/ml, 1.85 µl, dissolved in distilled water immediately prior to use). After 2 hours of incubation on ice, the reaction mixture was dialyzed against PBS overnight to remove free biotin. The biotinylated antibodies were stored at 4° C.

FACTT Reaction:
A typical FACTT assay requires a pair of antibodies for each antigen in a Sandwich type of detection. Generally the capture antibody was coated in Carbonate-Bicarbonate buffer (pH9.6) to a 384-well plate at 5 µg/ml and 15 µl/well for overnight at 4° C. A serial dilutions of antigens in the presence of FBS (0.1% for all samples including controls), were added to the coated plate. 15 µl of diluted biotinylated detection antibody (180 ng/ml) was used for each well. Streptavidin and biotin-DNA template (the amplification module, AM) were added sequentially at 5 μg/ml and 250 ng/ml respectively. We washed the plate six times with PBST (0.1% Tween20 in PBS) between each binding incubation. After excess AM and proteins were removed by washing, a 20 μl of reaction mixture (containing 60 units of T7 RNA polymerase plus (Ambion), 1.25 μM NTP, 1×T7 buffer (Ambion)) was added to each well. RNA amplification was performed at 37° C. for 3 hours. The RNA intercalating dye, RiboGreen (Molecular Probes) was added to the reaction mixture (20 μl, 1:200 diluted in the TE buffer supplied by the manufacturer) and the plate is read at Ex 485 nm/Em 535 nm in a TECAN Spectra Fluora reader. In the case of streptavidin detection, streptavidin was coated directly to a 384-well plate with the Carbonate-Bicarbonate buffer at different concentrations. The plate was then blocked with casein and then exposed to AM. After that, the standard FACTT protocol was followed.

ELISA:

ELISAs were also performed to compare sensitivity patterns with FACTT. A protocol similar to FACTT was followed to capture the antigen to the plate, except that the 96-well plate was used in ELISA and four-fold volume of IDAT reagents were used. For p185her2/neu, unlabelled h4D5 was used as the detection antibody and followed by six-time washing with PBST and incubation with the HRP conjugated anti-mouse secondary antibody (Pierce, 1:5,000 dilution). For the streptavidin detection, only biotinylated HRP was used as the secondary antibody (Zymed, 1:1000 dilution). Following washing again six times with PBST, 100 μl of TMB substrate (0.1 mg/ml, 0.05M phosphate-citrate buffer, pH 5.0) was incubated in each well at room temperature. The reaction was stopped within 15 minutes with 20 μl of 2M $H_2SO_4$ and the data was collected at 450 nm (absorbance filter) using the TECAN Spectra Fluora reader.

Mice:

NCR homozygous athymic (nude) mice (six to eight weeks-old) were purchased from the National Cancer Institute. $1\times10^6$ transformed T6-17 cells were suspended in 100 μl of PBS and injected subcutaneously into the flank of each animal. Animals were maintained in accordance with guidelines of the Institutional Animal Care and Use Committee (IACUC) of the University of Pennsylvania. Tumor volume was calculated by the formula:

π*length*width*Height/6.

Statistical Analysis:

The cut-off line for detection is defined as 3 SD (Standard deviation) over the background or control. The lowest concentration of analyte in a serial dilution showing dose-dependent readout is considered as the detection limit. Student's t test was used to calculate statistical difference of experimental vs control values. Difference is considered statistically significant if P<0.05. Prism program (GraphPad software Inc.) was used to analyze the correlation and draw the standard curve to calculate the concentration of antigens.

What is claimed is:

1. A method for detecting molecules expressing a selected epitope in a sample comprising:

(a) immobilizing a molecule expressing a selected epitope in a sample to a solid support;

(b) contacting the solid support with a molecule that specifically binds to the selected epitope, streptavidin and a biotinylated oligonucleotide that comprises an RNA polymerase promoter, wherein the molecule that specifically binds to the selected epitope is a monoclonal antibody that comprises a universal epitope, a FAb that comprises a universal epitope, a F(Ab)$_2$ that comprises a universal epitope, humanized or chimeric antibody that comprises a universal epitope, a single chain Fv that comprises a universal epitope, a constrained epitope specific CDR that comprises a universal epitope, a CDR mimetic that comprises a universal epitope, or a engineered CDR structure that comprises a universal epitope, wherein the solid support is additionally contacted with a biotinylated molecule that binds to the universal epitope, wherein the biotinylated molecule that binds to the universal epitope is a biotinylated monoclonal antibody, a biotinylated FAb, a biotinylated F(Ab)$_2$, a biotinylated humanized or chimeric antibody with or without a human Fc a biotinylated single chain Fv, a biotinylated constrained epitope specific CDR, a biotinylated CDR mimetic, or a biotinylated engineered CDR structure, whereby the molecule that specifically binds to the selected epitope also binds to the selected epitope of the molecule immobilized to the solid support and to the biotinylated molecule that binds to the universal epitope which binds to the streptavidin which binds to the biotinylated oligonucleotide that comprises an RNA polymerase promoter;

(c) amplifying the oligonucleotide by RNA amplification to produce an RNA amplification product that is not labeled with a radioactive label or a fluorescent label;

(d) contacting said amplified oligonucleotide with a fluorescent dye which stains the RNA amplification product; and (e) detecting fluorescence emitted from the stained RNA amplification product that allows linear quantification of the molecule comprising the selected epitope being present in the sample.

2. The method of claim 1 wherein the molecule comprising the selected epitope present in the sample is quantified by measuring fluorescence emitted from the stained RNA amplification product whereby the amount of fluorescence emitted is correlated to the amount of the molecule comprising the selected epitope present in the sample.

3. The method of claim 1 wherein the oligonucleotide is double stranded DNA.

4. The method of claim 1 wherein the solid support is a chip, bead or surface in a well of a multi-well plate.

5. The method of claim 1 wherein the solid support comprises an immobilized molecule that binds to the molecule that expresses the selected epitope.

6. The method of claim 1 wherein the fluorescent dye is an unsymmetrical cyanine dye.

* * * * *